US012575776B2

(12) United States Patent
Stoica et al.

(10) Patent No.: US 12,575,776 B2
(45) Date of Patent: Mar. 17, 2026

(54) COATED NOBLE METAL ELECTRODES

(71) Applicant: Heraeus Deutschland Gmbh & Co. KG, Hanau (DE)

(72) Inventors: Leonard Stoica, Hanau (DE); Ilias Nikolaidis, Hanau (DE)

(73) Assignee: Heraeus Medevio GmbH & Co. KG, Hanau (DE)

( * ) Notice: Subject to any disclaimer, the term of this patent is extended or adjusted under 35 U.S.C. 154(b) by 409 days.

(21) Appl. No.: 18/194,089

(22) Filed: Mar. 31, 2023

(65) Prior Publication Data

US 2023/0320646 A1 Oct. 12, 2023

(30) Foreign Application Priority Data

Apr. 7, 2022 (DE) .......................... 102022108481.7

(51) Int. Cl.
*A61B 5/268* (2021.01)

(52) U.S. Cl.
CPC .................................... *A61B 5/268* (2021.01)

(58) Field of Classification Search
CPC ............ A61B 5/268; A61B 2562/0215; A61B 2562/125
See application file for complete search history.

(56) References Cited

FOREIGN PATENT DOCUMENTS

| CN | 110124664 A | * | 8/2019 | .............. B01J 23/42 |
| EP | 3906964 A1 | | 11/2021 | |
| WO | 2015031265 A1 | | 3/2015 | |
| WO | WO-2021058154 A1 | * | 4/2021 | .............. C23C 18/08 |

OTHER PUBLICATIONS

Long-Term Stable Adhesion for Conducting Polymers in Biomedical Applications: IrOx and Nanostructured Platinum Solve the Chronic Challenge (Year: 2017).*

Ganti et al., A Comparison of Porosity Analysis Using 2D Stereology Estimates and 3D Serial Sectioning for Additively Manufactured Ti 6Al 2Sn 4Zr 2Mo Alloy, Practical Metallography, vol. 54, Issue 2 (2017), DOI: 10.3139/147.110432, , Carl Hanser Verlag Gmbh & Co. KG.

Giurlani et al., Measuring the Thickness of Metal Coatings: A Review of the Methods, Coatings 2020, 10, 1211; doi:10.3390/coatings10121211, Dec. 11, 2020, MDPI.

* cited by examiner

*Primary Examiner* — Eun Hwa Kim
(74) *Attorney, Agent, or Firm* — Dicke, Billig & Czaja, PLLC

(57) ABSTRACT

The invention relates to a medical electrode comprising a substrate, a first layer, and a second layer, wherein the first layer is arranged directly on the substrate, and the second layer is arranged directly on the first layer, wherein the first layer comprises a noble metal, and the second layer comprises a conductive polymer, wherein the first layer comprises a rough and/or porous surface.

15 Claims, 4 Drawing Sheets

20 μm

1 μm

COATED NOBLE METAL ELECTRODES

CROSS-REFERENCE TO RELATED APPLICATIONS

This application claims priority pursuant to 35 U.S.C. 119(a) to German Application No. 102022108481.7, filed Apr. 7, 2022, which application is incorporated herein by reference in its entirety.

FIELD OF THE INVENTION

The present invention relates to the field of medical technology, in particular medical electrodes for use in therapeutic and diagnostic methods.

TECHNICAL BACKGROUND

Medical electrodes can be coated with electrically conductive polymers to provide, for example, a softer surface and/or improved electrical properties. Such coated electrodes are described, for example, in WO 2015/031265 A1.

Preferred Embodiments

The object of the present invention is to provide improved coated medical electrodes and methods for the production thereof. For example, the invention enables coatings with improved mechanical stability. Furthermore, the present invention provides electrodes with improved electrical properties, such as high charge storage capacity and low impedance.

These objects are achieved by the methods and devices described herein, in particular those that are described in the claims.

Preferred embodiments of the invention are described below.

1. A medical electrode comprising a substrate, a first layer and a second layer, wherein the first layer is arranged directly on the substrate, and the second layer is arranged directly on the first layer, wherein the first layer comprises a noble metal, and the second layer comprises a conductive polymer, characterized in that the first layer comprises one or more of the following features (a) to (e):
(a) an open-pore structure,
(b) a porosity of at least 30% by volume,
(c) a density of at most 90% of the theoretical density of the noble metal,
(d) a specific surface area of at least $1 \times 10^6$ m$^{-1}$,
(e) an average surface roughness Ra of at least 500 nm.
2. The medical electrode according to embodiment 1, wherein the first layer further comprises one or more of the following features:
a charge storage capacity of at least 10 mC/cm$^2$,
an impedance of at most 1500 $\Omega$,
wherein the specified features are to be determined on an area of the first layer of 5 mm$^2$, and in the absence of the second layer.
3. The medical electrode according to any one of the preceding embodiments, wherein the substrate comprises a noble metal or a biocompatible plastics material.
4. The medical electrode according to any one of the preceding embodiments, wherein the first layer comprises a noble metal that is selected from the group consisting of platinum, iridium, palladium, gold, ruthenium, and rhodium.
5. The medical electrode according to any one of the preceding embodiments, wherein the second layer comprises PEDOT.
6. The medical electrode according to any one of the preceding embodiments, wherein the first layer covers at least 5% of the surface area of the substrate.
7. The medical electrode according to any one of the preceding embodiments, wherein the second layer intercalates with the first layer.
8. The medical electrode according to any one of the preceding embodiments, wherein the second layer comprises an edge that is covered by a third layer.
9. The medical electrode according to any one of the preceding embodiments, wherein the first layer can be produced by thermal decomposition of a particle-free noble metal ink.
10. A method for producing a medical electrode, comprising the steps of:
provision of a substrate,
application of a particle-free noble metal ink to the substrate,
thermal decomposition of the noble metal ink in order to obtain a first layer of noble metal,
application of a conductive polymer to the first layer in order to obtain a second layer.
11. The method according to embodiment 10, wherein the noble metal ink comprises an organic noble metal complex having diolefin and C6-C18 monocarboxylate ligands of the type $[LPd[O(CO)R1]X]_n$, $[LRh[O(CO)R1]]_m$ or $[LIr[O(CO)R1]]_m$, wherein L is a compound acting as a diolefin ligand, wherein X is selected from bromide, chloride, iodide and —O(CO)R2, wherein —O(CO)R1 and —O(CO)R2 denote identical or different non-aromatic C6-C18 monocarboxylic acid functional groups, and wherein n is an integer $\geq 1$ and m is an integer $\geq 2$.
12. The method according to embodiment 11, wherein the noble metal complex is a compound of the formula $[(L1L2)Pt[O(CO)R^1]_2]_n$, wherein n is equal to 1 or 2, L1L2 is cyclooctadiene or norbornadiene, and wherein R$^1$ is a non-aromatic C7-C17 hydrocarbon functional group.
13. The method according to any one of embodiments 10 to 12, wherein the noble metal ink comprises a solvent, which preferably comprises propylene glycol n-propyl ether and/or ethanol.
14. The method according to any one of embodiments 10 to 13, wherein a plurality of layers of a noble metal are successively applied, each by means of a particle-free noble metal ink.
15. The method according to any one of embodiments 10 to 14, wherein the noble metal ink/inks is/are applied by means of inkjet printing, screen printing, stamp printing, dispensing, dip coating, spray coating or spin coating.

DETAILED DESCRIPTION

Figure 1:
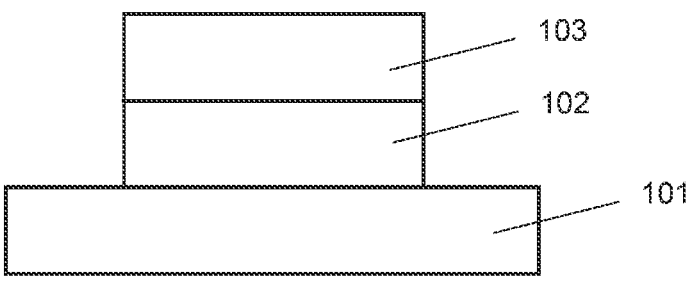
FIG. 1 shows an example of an embodiment of an electrode according to the invention in a cross-sectional view.

In principle, for the embodiments described herein, the elements of which "contain" or "comprise" a particular feature (e.g., a material), a further embodiment is always considered in which the element in question consists of that feature alone, i.e., comprises no further components. The word "comprise" or "comprising" is used herein synonymously with the word "contain" or "containing."

If an element is referred to in the singular in an embodiment, an embodiment is also being considered in which several of these elements are present. The use of a term for an element in the plural fundamentally also encompasses an embodiment in which only a single corresponding element is contained.

Unless otherwise indicated or clearly precluded from the context, it is possible in principle, and is herewith clearly taken into consideration, that features of different embodiments may also be present in the other embodiments described herein. It is also contemplated in principle that all features that are described herein in conjunction with a method are also applicable to the products and devices described herein, and vice versa. Only for reasons of succinct presentation are all such contemplated combinations not explicitly listed in all instances. Technical solutions which are known to be equivalent to the features described herein are also intended to be encompassed in principle by the scope of the invention.

A first aspect of the invention relates to a medical electrode comprising a substrate, a first layer, and a second layer, wherein the first layer is arranged directly on the substrate, and the second layer is arranged directly on the first layer, wherein the first layer comprises a noble metal, and the second layer comprises a conductive polymer, wherein the first layer has a rough and/or porous structure.

This may mean, for example, that the first layer comprises one or more of the following features (a) to (e):

(a) an open-pore structure, (b) a porosity of at least 30% by volume, (c) a density of at most 90% of the theoretical density of the noble metal, (d) a specific surface area of at least $1 \times 10^6$ $m^{-1}$, (e) an average surface roughness Ra of at least 500 nm.

The medical electrode can be configured for implantation, for example into the human or animal body. In one embodiment, the medical electrode is configured for direct tissue contact. In one embodiment, the medical electrode is biocompatible. The electrode can be configured to deliver an electrical signal to the human body. The electrode can be configured to receive an electrical signal from the human body.

The electrode comprises a substrate that is used as a base body and to support the first layer. The electrode can comprise a flexible substrate, for example made of plastics material. The substrate can, for example, be a polymer film, for example a film made of PTFE or polyimide. The substrate may comprise an electrically conductive surface, for example a metal surface. The substrate can comprise a wire, for example a metal wire. The substrate can be structured and contain, for example, one or more contact elements, one or more conductor tracks, and an electrical element configured to receive and/or output an electrical signal.

The electrode can furthermore comprise an encapsulation. The encapsulation can comprise a biocompatible material, such as platinum, titanium or a medical grade silicone. The encapsulation can comprise a feedthrough, such that the active part of the electrode can be led out of the encapsulation. In one embodiment, only the active part of the design protrudes from the encapsulation. The active part can comprise a part of the substrate and the first layer and second layer situated thereon.

The substrate preferably comprises a smooth surface, particularly at the interface between the substrate and the first layer. Therefore, in some embodiments, the substrate does not comprise a rough and/or porous structure, in particular does not comprise features (a) through (e) above.

The substrate can be a partial region of a medical electrode that serves as a support layer for the first layer. The substrate can be electrically insulating or electrically conductive. In some embodiments, the substrate comprises both electrically insulating and electrically conductive elements.

The substrate can comprise a biocompatible metal. Suitable biocompatible metals are known in the art, for example Pt, Ir, Ta, Pd, Ti, Fe, Au, Mo, Nb, W, Ni, Ti or a mixture or alloy thereof. Whether a metal is biocompatible can be determined using the EN ISO 10993 standard.

In some embodiments, the substrate comprises or consists of alloy MP35, PtIr10, PtIr20, 316L, 301, 304 or nitinol. The substrate can also include multilayer material systems. In some embodiments, the substrate consists of one or more of these materials.

MP35 is a nickel-cobalt-based hardenable alloy. A variant of MP35 is described in industry standard ASTM F562-13. In one embodiment, MP35 is an alloy comprising 33 to 37% Co, 19 to 21% Cr, 9 to 11% Mo, and 33 to 37% Ni.

PtIr10 is an alloy of 88 to 92% platinum and 8 to 12% iridium.

PtIr20 is an alloy of 78 to 82% platinum and 18 to 22% iridium.

316L is an acid-resistant CrNiMo austenitic steel with approximately 17% Cr; approximately 12% Ni, and at least 2.0% Mo. A variant of 316L is described in industry standard 10088-2. In one embodiment, 316L is an alloy comprising 16.5 to 18.5% Cr; 2 to 2.5% Mo, and 10 to 13% Ni.

301 is a chromium-nickel steel with high corrosion resistance. A variant of 301 is described in industry standard DIN 1.4310. In one embodiment, 301 is an alloy comprising 16 to 18% Cr and 6 to 8% Ni.

304 is an austenitic, acid-resistant 18/10 Cr—Ni steel described, for example, in the ASTM A213, ASTM A269, ASTM A312 or ASTM A632 manufacturing standards. 304 typically contains 8-10.5% nickel, 18-20% chromium, up to 2% manganese and up to 0.08% carbon. A variant of 304 is 304L, which contains up to 12% by weight of nickel.

Nitinol is a shape-memory nickel-titanium alloy having an ordered cubic crystal structure and a nickel content of approximately 55%, the remaining portion consisting of titanium. Nitinol has good biocompatibility and corrosion-resistance properties.

Unless otherwise indicated, all percentages given herein are to be understood as weight percent (wt. %).

Examples of biocompatible polymers include polyimide, polyethylene, polyurethane and silicone. In one embodiment, the substrate comprises polyimide, such as Kapton.

A first layer comprising a noble metal is arranged on the substrate. Examples of noble metals are platinum, iridium, palladium, gold, ruthenium and rhodium. In one embodiment, the noble metal is selected from the group consisting of platinum, iridium, palladium, gold and rhodium. The noble metal can also be a noble-metal-containing alloy, such as a platinum-iridium alloy. Examples of a platinum-iridium alloy are PtIr10 and PtIr20. In one embodiment, the first layer comprises, or consists of, platinum. In some embodiments, the first layer is free of non-noble metals or free of non-metals.

According to the invention, the first layer comprises a rough and/or porous surface. For example, this can be represented by one or more of the following properties:

an open-pore structure, a porosity of at least 30% by volume, a density of at most 90% of the theoretical density of the noble metal, a specific surface area of at least $1 \times 10^6$ m$^{-1}$, determined, for example, according to ISO 9277:2010, a mean surface roughness Ra of at least 500 nm, determined, for example, according to DIN EN ISO 25178-6:2010-06.

Due to these properties, better bonding of the first layer with the second layer can be achieved. As a result, the stability of the first layer and/or the second layer on the substrate can be improved. In addition, the aforementioned surface properties of the first layer can lead to improved electrical properties of the medical electrode according to the invention.

The first layer can have an open-pore structure. This means that the first layer resembles the shape of a sponge. In this case, there are interstices between the material of the first layer, a noble metal. In an open-pore structure, these interstices are interconnected. The interstices may be filled with another material, such as the material from which the second layer is formed.

The first layer can have a high porosity. For example, the first layer can have a porosity of at least 30 volume percent (vol. %, i.e., vol/vol). In some embodiments, the first layer has a porosity of at least 30, 40 or at least 50 volume percent.

The first layer can have a high surface roughness. For example, the first layer can have an average surface roughness Ra of at least 500 nm. In some embodiments, the first layer has an average surface roughness Ra of at least 500 nm, 600 nm, 700 nm, 800 nm, 900 nm, 1000 nm, 1500 nm, 2000 nm or at least 3000 nm. The surface roughness can be determined according to DIN EN ISO 25178-6:2010-06.

In particular, the first layer according to the invention can serve as a particularly advantageous support layer for the second layer. For example, conductive polymer compositions containing PEDOT, such as Amplicoat®, have particularly good adhesion on the first layer according to the invention, in particular compared to conventional metal surfaces. The combination of first layer and second layer according to the invention can simultaneously combine special advantages of improved electrical properties and mechanical stability.

In some embodiments, the first layer comprises recesses on its surface that are filled with the polymer of the second layer. In this manner, the first layer and the second layer can be interlocked.

In some embodiments, the first layer comprises porous cavities that are filled with the polymer of the second layer.

Without wanting to commit themselves to a particular theory, the inventors explain the improvement in stability due to the structure of the electrode according to the invention as follows:

The mechanical stability of the first layer on the substrate results from the sum of the local molecular adhesion forces at the polymer-metal interface and is thus proportional to the active area of the electrode. For an electrode surface with a certain roughness, the active area of the electrode is a multiple (for example >5×) of the geometric area of the electrode surface. Thus, a rough electrode surface has a greater number of molecular anchors between the polymer film and the Pt substrate. In one example case, an electrode according to the invention has a >10-fold higher active electrode area compared to a flat Pt substrate, such that such electrode modification leads to a proportional increase in adhesion forces between the polymer and the Pt substrate, which means improved mechanical stability. The roughness factor of the electrode according to the invention increases, if necessary, with increasing substrate coverage.

In addition to the contribution of the roughness factor to the improved adhesion forces of the film described above, the geometrically non-uniform distribution of the noble metal structures produced according to the invention on the substrate surface area additionally leads to a synergistic effect with respect to the mechanical stability of the polymer, which is based on the complementary steric filling of the porous structure of the first layer according to the invention with the polymer of the second layer, and the interpenetration between metal and polymer material.

This particular synergistic combination of roughness and irregular geometry of the electrode produced according to the invention (steric effect) results in particularly improved polymer stability.

In addition, the fine surface structure of the first layer is protected from damage by being covered with the second layer.

In some embodiments, the electrodes according to the invention are characterized by improved electrical properties. For example, the first layer can have a charge storage capacity of at least 10 mC/cm$^2$, or can have a charge storage capacity of at least 20, 30, 40, 50, 60, 70, 80, 90 or 100 mC/cm$^2$.

In some embodiments, the first layer can have an impedance of at most 1500Ω. Preferably, the first layer can have an impedance of at most 1400, 1300, 1200, 1100, 1000, 900, 800, 700, 600, 500, 400, 300, 200 or at most 100Ω.

The charge storage capacitance and impedance of the first layer specified herein shall each be determined on an area of the first layer of 5 mm$^2$. The determination should be made on an exposed first layer, i.e., in the absence of a second layer.

The first layer can have a large specific surface area. Preferably, the first layer has a specific surface area of at least $1 \times 10^6$ m$^{-1}$, more preferably at least $1 \times 10^7$ m$^{-1}$, and most preferably at least $1 \times 10^8$ m$^{-1}$. The specific surface area can be determined, for example, according to ISO 9277:2010. Herein, as Example 5, a method for determining the specific surface area is described.

A second layer comprising a conductive polymer is arranged on the first layer. Herein, "conductive polymer" means an electrically conductive polymer. In one aspect of the invention, it is preferred that the electrically conductive polymer comprises poly(3,4-ethylenedioxythiophene) (PEDOT) or a functionalized derivative thereof. For example, the electrically conductive polymer can be derived from 3,4-ethylenedioxythiophene (EDOT).

In one aspect of the invention, it is preferred that the electrically conductive polymer is derived from a functionalized derivative of EDOT, which is selected from the group consisting of hydroxymethyl EDOT, EDOT vinyl, EDOT ether allyl, EDOT COOH, EDOT MeOH, EDOT silane, EDOT vinyl, EDOT acrylate, EDOT sulfonate, EDOT amine, EDOT amide and combinations thereof. For example, the functionalized derivative of 3,4-ethylenedioxythiophene (EDOT) can be selected from the group consisting of hydroxymethyl EDOT, EDOT vinyl, EDOT ether allyl, EDOT acrylate and combinations thereof.

In one aspect of the invention, it is preferred that the electrically conductive polymer contains an anionic photoreactive crosslinking agent. In this aspect, it is preferred that the crosslinking agent comprises at least two photoreactive groups. In a further aspect of the invention, it is preferred that the anionic photoreactive crosslinking agents comprise a compound of Formula I:

Xi~Y~X2 wherein Y is a functional group containing at least one acidic group or salt of an acidic group; and Xi and X2 are each independently a functional group containing a latent photoreactive group. Examples of a photoreactive group are an aryl ketone or a quinone. In a further aspect of the invention, it is preferred that spacers are part of Xi or X2, preferably together with the latent photoreactive group.

In one aspect of the invention, it is preferred that, in the compound of Formula I, Y is a functional group comprising at least one acidic group or salt thereof. Examples of acidic groups include sulfonic acids, carboxylic acids, phosphonic acids and the like. Examples of salts of such groups are sulfonate, carboxylate and phosphate salts. As an example, the crosslinking agent can contain a sulfonic acid or sulfonate group. In a further aspect of the invention, it is preferred that such a photoreactive crosslinking agent is anionic. Examples of counterions are alkali and alkaline earth metals, ammonium, protonated amines and the like.

In one aspect of the invention, it is preferred that the electrically conductive polymer comprises an anionic photoreactive hydrophilic polymer. In this aspect, it is preferred that the hydrophilic polymer is anionic. Examples of anionic hydrophilic polymers include homopolymers, copolymers, terpolymers and the like. In a further aspect of the invention, it is preferred that the anionic hydrophilic polymer is derivatized with photoreactive groups if the electrically conductive polymer comprises at least one anionic hydrophilic polymer.

In a further aspect of the invention, it is preferred that the anionic hydrophilic polymer comprises polymers containing polyacrylamide and photoreactive groups ("photo-PA"). In a further aspect of the invention, it is preferred that the anionic hydrophilic polymer comprises polyacrylamide and sulfonate groups. For example, the anionic hydrophilic polymer comprises acrylamido-2-methylpropane sulfonate (AMPS) groups and polyethylene glycol segments.

The terms "latent photoreactive group" and "photoreactive group" are used interchangeably and refer to a chemical entity that is sufficiently stable to remain in an inactive state (i.e., ground state) under normal storage conditions, but which can undergo a transformation from the inactive state to an activated state if exposed to a suitable energy source. Unless otherwise specified, the reference to photoreactive groups preferably also includes the reaction products of the photoreactive groups.

In one aspect of the invention, it is preferred that the photoreactive groups are selected to be responsive to different parts of the actinic radiation. For example, groups can be selected to be photoactivated with either ultraviolet or visible radiation. Examples of photoreactive groups include azides, diazos, diazirines, ketones and quinones. In a further aspect of the invention, it is preferred that the photoreactive group comprises an aryl ketone, such as acetophenone, benzophenone, anthrone, and anthrone-like heterocycles (i.e., heterocyclic analogs of anthrone, such as those with N, O or S at the 10-position), or substituted (e.g., ring-substituted) derivatives thereof. Examples of aryl ketones include heterocyclic derivatives of anthrone, including acridone, xanthone, and thioxanthone, as well as their ring-substituted derivatives. Other suitable photoreactive groups are quinones, such as anthraquinone.

Electrically conductive polymers are known to those skilled in the art and are commercially available under the brand names Orgacon®, available from Agfa-Gevaert N.V. (Belgium), or Amplicoat®, available from Heraeus Deutschland GmbH & Co. KG (Germany). Further examples of electrically conductive polymers, along with methods for applying them to substrates, are described in WO 2015/031265 A1, which is hereby incorporated by reference in its entirety.

In a further aspect of the invention, it is preferred that the second layer comprises a biocompatible polymer. In a further aspect of the invention, it is also preferred that the second layer is hydrophilic. A "hydrophilic" material is defined as one that has a water contact angle of less than 90°.

In a further aspect of the invention, it is preferred that the second layer has a water contact angle that is in the range of 10° to 30°, preferably in the range of 15° to 25° and more preferably in the range of 19° to 22°. In a further aspect of the invention, it is preferred that the second layer has a surface energy that is in the range of 35 mN/m to 55 mN/m, more preferably in the range of 40 mN/m to 50 mN/m and further preferably in the range of 42 mN/m to 46 mN/m.

Other suitable conductive polymers are described, for example, in WO 2015/031265 A1, which is hereby incorporated by reference.

In some embodiments, the thickness of the first layer is at least 100 nm, further preferably at least 200, 300, 400 or 500 nm. In some embodiments, the thickness of the first layer is approximately 200 to 800 or approximately 100 to 1000 nm.

In some embodiments, the first layer is sufficiently thick to form a closed layer on the substrate.

In some embodiments, the thickness of the second layer is at least 300 nm, more preferably at least 400, 500, 600, 700, 800, 900 or 1000 nm. In some embodiments, the thickness of the second layer is approximately 500 to approximately 1000 nm or approximately 800 to 2000 nm.

The thickness of the respective layers (for example, the first layer and the second layer) can be determined by evaluating cross-sectional electron microscopy images, wherein the average distance between the profile lines along the opposing interfaces of a layer to be determined is calculated using suitable image processing software. More details on the determination of coating thickness by means of electron microscopy are described in Giurlani et al, Coatings 2020, 10, 1211; doi:10.3390/coatings10121211.

In some embodiments, the first layer covers at least 5% of the surface area of the substrate. It is meant by this that a region of the substrate covered with the first layer has a surface area coverage of at least 5%. When determining this value, completely free regions of the substrate are not taken into account. This embodiment refers to a first layer that is not continuously closed, but comprises free regions on a microscopic size scale. For example, such a layer can have a disordered, mesh-like or spongy structure formed from a noble metal. Particularly advantageous properties of the first layer can be achieved if this mesh-like structure is substantially continuous; i.e., the first layer comprises structures that are interconnected over substantially the entire area of the first layer. This is to be demarcated from a first layer which is merely formed from individual noble metal particles that do not touch each other. Not comprised in this embodiment of a first layer are completely closed and smooth noble metal layers which in their structure resemble, for example, a surface of mica. In this sense, the first layer can also cover more than 10%, 15%, 20%, 25% or more than 30% of the surface area of the substrate.

The portion of the substrate surface area covered by the first layer can be determined based on electron micrographs using image processing software such as ImageJ (Rasband, W. S., ImageJ, U. S. National Institutes of Health, Bethesda, Maryland, USA, https://imagej.nih.gov/ij/, 1997-2018). For this purpose, the images should cover a range of approximately 50 to 150 μm in length. The aim here is to achieve the highest possible contrast between the substrate and the first layer. To evaluate the images, these gray scale images can be converted into binary images using the Otsu method. This means that the image pixels are in each case assigned to the substrate or the first layer by means of a threshold value. Then, using the binary images, the surface area can be determined as the quotient of the number of pixels representing the first layer and the total number of pixels per image.

In some embodiments, the second layer intercalates with the first layer. This means that the material of the second layer fills substantially all the interstices and cavities of the first layer, such that there is an interpenetrating, closed composite of two different materials.

To further improve the stability of the electrode, the edge of the second layer can be protected by applying a third layer to the edge of the second layer. As used herein, "edge" of the second layer means the lateral end or lateral edge of the second layer, not the entire remaining surface of the second layer facing outward in the direction away from the substrate. For example, the edge of the second layer can be covered with a polymer layer. Preferably, the second layer should not be completely covered, but as large a part of the second layer as possible should remain freely accessible to the outside, such that the third layer influences the electrical properties of the electrode as little as possible. With the aid of the arrangement of a third layer described above, the adhesion of the first and/or second layer to the substrate can be improved.

Noble metal layers that can be produced using the methods and compositions described herein (also referred to herein as "noble metal inks") have been shown to be particularly advantageous for the first layer. Preferably, particle-free noble-metal-containing compositions are applied to the substrate and a rough and/or porous metal layer is formed on the substrate by thermal decomposition of the noble metal complexes contained therein. Preferred noble metal complex compounds that are soluble in an organic solvent can be used for this purpose. Particle-free noble metal inks are characterized by better usability with printing techniques such as inkjet printing compared to particle-containing compositions. In addition, such inks spread highly homogeneously on the substrate surface area, thus leading to the formation of particularly homogeneous noble metal layers on the substrate.

Accordingly, some embodiments of the electrode described herein include a first layer that can be produced using one of the noble metal complex compounds described herein. In some embodiments of the electrodes described herein, the first layer can be produced by thermal decomposition of a noble metal ink described herein.

A preferred noble metal complex compound for preparing the first layer according to the invention comprises at least one central noble metal atom, which is complexed by one or more organic ligands through one or more free electrode pairs.

The organic noble metal complex compound is preferably soluble in a solvent, for example an organic solvent or solvent mixture suitable for inkjet printing processes. For this purpose, the organic noble metal complex compound can comprise a hydrocarbon functional group having 7 to 17 carbon atoms, preferably 7 to 10 carbon atoms. The organic noble metal complex compound can also comprise several such hydrocarbon functional groups. The noble metal complex compounds described below are characterized by particularly good solubility in various solvents, which are compatible with inkjet printing processes, for example, and also wet substrates with low polarity, such as polyimide, well.

For example, the organic noble metal complex compound can comprise a platinum complex of the type $[L1L2Pt[O(CO)R1]X]_n$, wherein L1 and L2 represent identical or different monoolefin ligands or together represent a compound L1L2 acting as a diolefin ligand, wherein X is selected from bromide, chloride, iodide, and —O(CO)R2, wherein —O(CO)R1 and —O(CO)R2 represent identical or different non-aromatic C8-C18 monocarboxylic acid functional groups, or together represent a non-aromatic C8-C18 dicarboxylic acid functional group —O(CO)R1R2(CO)O—, wherein said platinum complexes are mononuclear platinum complexes with n=1, or wherein, in the event of the presence of L1L2 and/or —O(CO)R1 R2(CO)O—, can be polynuclear platinum complexes with a whole number n>1.

The organic noble metal complex compound can comprise noble metal complexes of palladium, rhodium and iridium, respectively, each with diolefin and C6-C18 monocarboxylate ligands. More specifically, noble metal complexes of the type $[LPd[O(CO)R1]X]_n$ or $[LM[O(CO)R1]]_n$ are provided, wherein L denotes a compound acting as a diolefin ligand, wherein M is selected from rhodium and iridium, wherein X is selected from bromide, chloride, iodide and —O(CO)R2, wherein —O(CO)R1 and —O(CO)R2 denote identical or different non-aromatic C6-C18 monocarboxylic acid functional groups, wherein they comprise mononuclear noble metal complexes with n=1 or multinuclear noble metal complexes with integer n>1.

The term "compound acting as a diolefin ligand" used herein refers to a compound which, in the noble metal complexes described herein, provides both of, or two of, its olefinic double bonds with a central noble metal atom to form a complex or with two central noble metal atoms in a bridging manner to form a complex.

In the case of polynuclear noble metal complexes described herein, the number n generally represents a whole number, for example in the range from 2 to 5. In other words, whole number n>1 is generally in the range from 2 to 5; in particular, n is in this case equal to 2 and the platinum complexes are dinuclear noble metal complexes. In particular, compound L acts as a bridging ligand in the multinuclear noble metal complexes described herein. X can also have a bridging effect.

In the embodiment of mononuclear palladium complexes of the $[LPd[O(CO)R1]X]_n$ type described herein, L is a compound acting as a diolefin ligand at the palladium central atom; X denotes bromide, chloride, iodide or —O(CO)R2; and —O(CO)R1 and —O(CO)R2 denote identical or different non-aromatic C6-C18 monocarboxylic acid functional groups.

In the embodiment of mononuclear noble metal complexes of the $[LM[O(CO)R1]]_n$ type described herein, L is a compound acting as a diolefin ligand at the noble metal central atom; M is rhodium or iridium; and —O(CO)R1 is a non-aromatic C6-C18 monocarboxylic acid functional group.

In a preferred embodiment of dinuclear or polynuclear noble metal complexes of the type $[LPd[O(CO)R1]X]_n$ described herein, L denotes a compound bridging different palladium centers acting as a diolefin ligand; X denotes bromide, chloride, iodide or —O(CO)R2; n denotes 2, 3, 4 or 5, preferably 2; and —O(CO)R1 and —O(CO)R2 denote identical or different non-aromatic C6-C18 monocarboxylic acid functional groups.

In a preferred embodiment of dinuclear or polynuclear noble metal complexes of the type $[LM[O(CO)R1]]_n$ described herein, L denotes a compound bridging different noble metal centers acting as a diolefin ligand; M denotes rhodium or iridium; n denotes 2, 3, 4 or 5, preferably 2; and —O(CO)R1 denotes a non-aromatic C6-C18 monocarboxylic acid functional group.

Examples of diolefins or compounds of the type L that are capable of acting as diolefin ligands include hydrocarbons, such as COD (1,5-cyclooctadiene), NBD (norbornadiene), COT (cyclooctatetraene), and 1,5-hexadiene, in particular COD and NBD. These are preferably pure hydrocarbons; however, the presence of heteroatoms, for example also in the form of functional groups, is also possible.

X can denote bromide, chloride, iodide or —O(CO)R2; it preferably denotes chloride or —O(CO)R2, in particular —O(CO)R2.

The non-aromatic monocarboxylic acid functional groups —O(CO)R1 and —O(CO)R2 in each case denote identical or different non-aromatic C6-C18 monocarboxylic acid functional groups. The term "non-aromatic" used in this context excludes purely aromatic monocarboxylic acid functional groups but not araliphatic monocarboxylic acid functional groups of which the carboxyl function(s) is/are bound to aliphatic carbon. Preferably, —O(CO)R1 and —O(CO)R2 denote identical non-aromatic C6-C18 monocarboxylic acid functional groups. Among the non-aromatic C6-C18 monocarboxylic acid functional groups, monocarboxylic acid functional groups having 8 to 18 carbon atoms, i.e., non-aromatic C8-C18 monocarboxylic acid functional groups, are preferred.

Examples of non-aromatic C6-C18 or the preferred C8-C18 monocarboxylic acids having the functional groups —O(CO)R1 or —O(CO)R2 include hexanoic acids, heptanoic acids, octanoic acids, nonanoic acids, and decanoic acids, to name but a few examples. Not only linear representatives but also those having branches and/or cyclic structures, such as 2-ethylhexanoic acid, cyclohexanecarboxylic acid, and neodecanoic acid, are included. The respective functional groups R1 and R2 bonded to a carboxyl group comprise 5 to 17 or even more preferably 7 to 17 carbon atoms.

Preferred examples of palladium complexes described herein include $[(COD)Pd[O(CO)R1]_2]_n$ and $[(NBD)Pd[O(CO)R1]_2]_n$, wherein n is 1 or 2 and in particular 1, and wherein R1 represents a non-aromatic C5-C17 hydrocarbon functional group.

Preferred examples of rhodium complexes described herein include $[(COD)Rh[O(CO)R1]]_n$ and $[(NBD)Rh[O(CO)R1]]_n$, wherein n is 1 or 2 and in particular 1, and wherein R1 represents a non-aromatic C5-C17 hydrocarbon functional group.

Preferred examples of iridium complexes described herein include $[(COD)Ir[O(CO)R1]]_n$ and $[(NBD)Ir[O(CO)R1]]_n$, wherein n is 1 or 2 and in particular 1, and wherein R1 is a non-aromatic C5-C17 hydrocarbon functional group.

In some embodiments of the noble metal complexes disclosed herein, a non-aromatic monocarboxylic acid functional group does not comprise a phenylacetic acid functional group.

In some embodiments of the noble metal complexes disclosed herein, R1 does not comprise benzyl. In some embodiments of the noble metal complexes disclosed herein, R2 does not comprise benzyl.

The noble metal complexes described herein can be easily produced by ligand exchange, in particular without using carboxylic acid silver salts in the process. The production method includes mixing and suspending or emulsifying a two-phase system. One phase here comprises a reactant of the type $[LPdX_2]_n$ or $[LRhX]_n$ or $[LIrX]_n$, in each case with X selected from bromide, chloride and iodide, preferably chloride, either as is or preferably in the form of an at least substantially water-immiscible organic solution of such a reactant. Examples of organic solvents that are suitable for producing such an organic solution and at least substantially water-immiscible also include oxygen-containing solvents, for example corresponding water-immiscible ketones, esters, and ethers, in addition to aromatics and chlorinated hydrocarbons, such as toluene, xylene, di-, tri-, and tetrachloromethane. In contrast, the other phase comprises, an aqueous solution of alkali metal salt (in particular sodium or potassium salt) and/or magnesium salt of a C6-C18 monocarboxylic acid of the type R1COOH and optionally additionally of the type R2COOH. The selection of the type of monocarboxylic acid salt(s) depends on the type of noble metal complex described herein which is to be produced or the combination of noble metal complexes described herein which is to be produced. The two phases are intensively mixed, for example by shaking and/or stirring, thereby forming a suspension or an emulsion. Mixing is performed for the purpose of maintaining the suspension or emulsion state, for example for a duration of 0.5 to 24 hours, for example at a temperature in a range from 20 to 50° C. The ligand exchange takes place in the process, the noble metal complex or complexes described herein formed dissolving in the organic phase, while the alkali metal X salt or $MgX_2$ salt that is likewise formed dissolves in the aqueous phase. Upon completion of the suspension or emulsification, organic and aqueous phase are separated from one another. The noble metal complex or complexes described herein formed can be obtained from the organic phase and, optionally, subsequently purified by means of conventional methods.

Examples of preferred noble metal complexes that may be used in connection with the present invention include the complex compounds $(COD)Pt[O(CO)CH(C_2H_5)C_4H_9]_2$ (also referred to herein as "PtE complex"), $(COD)Pt[O(CO)C(CH_3)_2C_6H_{13}]_2$ (also referred to herein as "PtV complex") and mixtures thereof.

A further aspect of the present invention relates to a method for producing coated medical electrodes.

In one embodiment, the method comprises the following steps:

provision of a substrate,
  application of a particle-free noble metal ink to the substrate,
  thermal decomposition of the noble metal ink in order to obtain a first layer of noble metal,
  application of a conductive polymer to the first layer in order to obtain a second layer.

In one embodiment, the noble metal ink comprises an organic noble metal complex having diolefin and C6-C18 monocarboxylate ligands of the type $[LPd[O(CO)R1]X]_n$, $[LRh[O(CO)R1]]_m$ or $[LIr[O(CO)R1]]_m$, wherein L denotes a compound acting as a diolefin ligand, wherein X is selected from bromide, chloride, iodide and —O(CO)R2, wherein —O(CO)R1 and —O(CO)R2 denote identical or different non-aromatic C6-C18 monocarboxylic acid functional groups, and wherein n is an integer≥1 and m is an integer≥2.

In one embodiment, the noble metal complex is a compound of the formula $[(L1L2)Pt[O(CO)R1]2]_n$, wherein n is equal to 1 or 2, L1L2 is cyclooctadiene or norbornadiene, and wherein $R^1$ is a non-aromatic C7-C17 hydrocarbon functional group.

Further, any of the noble metal complexes shown hereinabove in connection with the electrode of the invention may be used.

In one embodiment, the noble metal ink comprises a solvent, which preferably comprises propylene glycol-n-propyl ether and/or ethanol. Further, any solvent and mixtures thereof shown above herein in connection with the electrode of the invention may be used.

In some embodiments, a plurality of layers of a noble metal are successively applied, each by means of a particle-free noble metal ink. For this purpose, a first layer of a particle-free noble metal ink can be applied first, and the ink can be dried until substantially no liquid remains on the substrate. The substrate is now coated with a solid layer of the noble metal complex contained in the ink. Optionally, the noble metal complex can be thermally decomposed in order to convert the noble metal complex into metallic noble metal. Alternatively, another layer of the noble metal ink can be applied directly, and all applied layers of the noble metal complex can be thermally decomposed together after all desired layers of the noble metal complex have been applied to the substrate. In this manner, layers of a noble metal having different thicknesses, which exhibit the properties described herein, can be applied to the substrate.

In one embodiment, a noble metal ink is applied by means of inkjet printing, screen printing, stamp printing, dispensing, dip coating, spray coating or spin coating. A plurality of different noble metal inks can also be applied by one or more of these mentioned methods. Some of these methods, in particular the printing methods mentioned, offer the advantage that any pattern of a noble metal can be applied to the substrate as the first layer. This facilitates the rapid and cost-effective production of a variety of electrodes, such as a multi-electrode array described herein.

A further aspect of the invention relates to the use of any of the methods as described herein for producing a medical electrode.

A further aspect of the invention relates to the use of the noble metal complex compounds and/or noble metal inks described herein for producing the medical electrodes described herein.

A further aspect of the invention relates to an electrode that can be produced by the methods described herein.

In a further aspect, an electrical medical device comprising an electrode according to any of the preceding aspects and embodiments thereof is provided.

The electrical medical device can be, for example, a lead, pulse generator, cardiac pacemaker, cardiac resynchronization device, sensor or stimulator. Leads are electrical wires which can be used, for example, in medical applications such as neuromodulation, cardiac stimulation, deep-brain stimulation, spinal-cord stimulation, or gastric stimulation. In one embodiment, the lead is configured and/or intended to be connected to a generator of an active implantable device. A lead can also be used in a medical device to receive an electrical signal. A stimulator is a medical device which can achieve a physiological effect by sending an electrical signal to the body of a living being. For example, a neuro-stimulator can, by delivering an electrical signal to a nerve cell, produce an electrical signal in the nerve cell (e.g. an action potential).

A further embodiment relates to a microelectrode array containing a plurality of electrodes according to the invention.

A further aspect relates to a diagnostic method in or on the body of a living being, comprising the recording of an electrical signal by means of the electrode described herein.

A further aspect relates to the use of the electrode described herein in a diagnostic method in or on the body of a living being, comprising the recording of an electrical signal by means of the electrode.

A further aspect relates to a therapeutic method in or on the body of a living being, comprising the delivery of an electrical signal by means of the electrode described herein.

A further aspect relates to the use of the electrode described herein in a therapeutic method in or on the body of a living being, comprising the delivery of an electrical signal by means of the electrode.

The therapeutic method can comprise the delivery of an electrical signal to nerve cells or muscle cells in the region of an organ, for example the heart, muscle, stomach or brain.

The diagnostic method can comprise the recording of an electrical signal from nerve cells or muscle cells in the region of an organ, for example, heart, muscle or brain.

Test Methods

Determination of Porosity

The pore volume and pore diameter distribution were determined with mercury porosimetry in accordance with ISO 15901-1:2016. The procedure was as follows: sample mass 30 mg; surface tension of mercury 0.48 N/m; contact angle of mercury 140°; instrument: Porotec Pascal 140+440; measurement method: scanning; start fill pressure 0.0128 MPa; diatometer: powder, small volume; sample preparation: 8 h at 110° C. under vacuum. In principle, the porosity is given herein in the unit of volume percent (vol/vol).

For very small areas and layer thicknesses, the porosity can be determined, if necessary, by electron micrographs using suitable image processing programs such as ImageJ, in a corresponding manner as described herein for surface area coverage. An example of such a measurement of porosity is described in Ganti et al, Pract. Metallogr. 54 (2017), DOI: 10.3139/147.110432.

Determination of the Specific Surface Area

The specific surface area corresponds to the ratio of the outer surface area (in $m^2$) of a body to the volume thereof (in $m^3$), wherein the size of the outer surface area is determined with nitrogen as adsorbate at 77 K in accordance with the BET theory (multipoint method, ISO 9277:2010).

Determination of Density

To determine density, the amount of deposited noble metal (e.g., platinum) is first determined gravimetrically. Subsequently, the volume of the deposited noble metal body is determined (by microscopy or—for determining the thickness of the layer—by scanning electron microscopy). The actual density thereof is determined from the ratio of the mass and the volume of the deposited noble metal body. In the case of platinum, a theoretical density of 21.45 $g/cm^3$ was assumed, and in the case of palladium, 11.99 $g/cm^3$.

EXAMPLES

The invention is further illustrated below using examples which are, however, not to be understood as limiting. It will be apparent to the person skilled in the art that other equivalent means may be similarly used in place of the features described here.

Production Example 1: Synthesis of the PtE Complex

A solution of 65 mmol of (COD)PtCl2 in 100 ml of dichloromethane was stirred, and a solution of 260 mmol of sodium 2-ethylhexanoate in 500 ml of water was added. The two-phase mixture was emulsified for 24 h at 20° C. by vigorous stirring. The dichloromethane phase turned yellow in the process. The dichloromethane phase was separated, and the solvent was distilled off. The viscous, yellow residue was absorbed into 150 ml petroleum benzine (40-60), and the solution was dried with magnesium sulfate and filtered. The petroleum benzine was then completely distilled off. A viscous yellow residue of (COD)Pt[O(CO)CH($C_2H_5$)$C_4H_9$]$_2$ remained.

To produce a printable ink containing the PtE complex dissolved in an organic solvent, the residue obtained above is dissolved at the desired concentration in a mixture of PnP and ethanol (1:1) in such an amount that the composition contains 10% by weight of platinum.

Production Example 2: Synthesis of the PtV Complex

A solution of 65 mmol (COD)PtCl2 in 100 ml dichloromethane was stirred, and a solution of 260 mmol sodium neodecanoate (Versatic™ Acid 10, Hexion Inc., Ohio, USA) in 500 ml water was added. The two-phase mixture was emulsified for 24 h at 20° C. by vigorous stirring. The dichloromethane phase turned yellow in the process. The dichloromethane phase was separated, and the solvent was distilled off. The viscous, yellow residue was absorbed into 150 ml petroleum benzine (40-60), and the solution was dried with magnesium sulfate and filtered. The petroleum benzine was then completely distilled off. A viscous yellow residue of (COD)Pt[O(CO)C($CH_3$)$_2$$C_6H_{13}$]$_2$ remained.

To produce a printable ink containing the PtV complex dissolved in an organic solvent, the residue obtained above is dissolved at the desired concentration in a mixture of PnP and ethanol (1:1) in such an amount that the composition contains 10% by weight of platinum.

Example 1: Production of a Coated Electrode on a Metal Substrate

Rectangles of 4 $cm^2$, which had a stem for contacting, were made from PtIr sheet. These PtIr coupons were cut with a laser into six rectangles of equal size with a total area of 60 $mm^2$ (3 mm×20 mm). The platinum ink according to production example 1 was applied to the PtIr coupons using the "Diamatix Materials Printer DMP-2850" inkjet printer. In some samples, 2 or 3 such layers were applied on top of each other, by which a uniform layer with a correspondingly higher thickness was formed. The printed substrates were cured for 5 minutes at 200° C. in a laboratory oven, forming a metallic platinum layer.

The platinum-coated surface areas were coated with Amplicoat® (Heraeus, Germany) according to the manufacturer's instructions.

Example 2: Production of a Coated Electrode on a Polyimide Substrate

The surface areas of several Kapton® films with a thickness of 0.075 mm made of polyimide (DuPont) were coated with a two-dimensional layer of platinum ink using an inkjet printer (DMP-2850, Fujifilm Europe GmbH) and the piezo inkjet method as described in production example 1. In some samples, 2 or 3 such layers were applied on top of each other, by which a uniform layer with a correspondingly higher thickness was formed. The printed polyimide substrates were cured for 5 minutes at 200° C. in a laboratory oven, forming a metallic platinum layer. These platinum layers were then coated with Amplicoat® (Heraeus, Germany) according to the manufacturer's instructions.

Example 3: Electrochemical Measurements

The electrodes produced in Example 1 were masked with a Kapton film. In each case, only the printed electrode surface area remained as an unmasked area. The size of the unmasked electrode surface areas was determined in each case using a reflected light microscope (DinoLight) and associated software (DinoCapture 2.0).

Samples were characterized electrochemically using silver/silver chloride electrodes in phosphate-buffered saline (PBS; pH 7.4).

The results are shown in Tab. 1 and Tab. 2 below

TABLE 1

Measurements of the samples according to example 1, first layer (porous platinum)

| Electrode | Surface area [$mm^2$] | Impedance \|Z\| [Ω] | Charge storage capacitance CSC, cathode phase [$mC/cm^2$] |
|---|---|---|---|
| 1 × PtE ink | 6.439 | 1052 | −19.95 |
| 2 × PtE ink | 6.415 | 648 | −24.95 |
| 3 × PtE ink | 5.658 | 396 | −55.64 |
| Bare PtIr | 5.557 | 21343 | −2.61 |

TABLE 2

Measurements of the samples according to example 1, after application of a layer of a conductive polymer (Amplicoat)

| Electrode | Surface area [$mm^2$] | Impedance \|Z\| [Ω] | Charge storage capacitance CSC, cathode phase [$mC/cm^2$] |
|---|---|---|---|
| Bare PtIr + Amplicoat | 5.557 | (not determined) | −5.47 |
| 1 × PtE ink + Amplicoat | 6.439 | 271 | −30.51 |
| 2 × PtE ink + Amplicoat | 6.415 | 233 | −40.84 |

TABLE 2-continued

Measurements of the samples according to example 1, after
application of a layer of a conductive polymer (Amplicoat)

| Electrode | Surface area [mm²] | Impedance \|Z\| [Ω] | Charge storage capacitance CSC, cathode phase [mC/cm²] |
|---|---|---|---|
| 3 × PtE ink + Amplicoat | 5.658 | 479 | −26.74 |

Example 4: Wipe Test

The stability of the samples according to Examples 3 and 4 was determined using a self-designed measuring device as follows. The device consisted of a sample table that could be displaced in depth and a stamp on which weights of 5 g per disk could be placed. The stamp was covered at the front with a foam previously soaked in PBS and was vertically movable with low frictional resistance due to a hole in the metal block. The stamp itself had a net weight of 33 g.

To carry out the test, the samples were fixed on the sample stage with polyimide adhesive tape at the beginning and the electrodes were moistened with PBS. The metal block was then aligned so that the foam of the stamp rested on the electrode. Through lateral movement of the sample stage($\triangleq$ 1 cycle) pressure was applied to the electrodes by friction. 10 cycles were carried out per weight. Subsequently, the weight was increased in 10 g increments for the next measurement. Visual inspection of the electrodes was carried out between each increase in weight. The measurement was repeated until approximately two-thirds of the coating had detached from the electrodes.

The results are shown in Tab. 3. The values shown there indicate in each case the highest tested load at which the coatings were still stable.

TABLE 3

Results of the wipe test on samples according to example 1.

| Electrode | Maximum load [g] |
|---|---|
| Bare PtIr + Amplicoat | 60 |
| 1 × PtE ink + Amplicoat | 30 |
| 2 × PtE ink + Amplicoat | 200 |
| 3 × PtE ink + Amplicoat | 200 |

Example 5—Determination of the Specific Surface Area

The specific surface area of the samples according to Example 2 (3 layers of PtE ink printed on polyimide substrate) was determined by cyclic voltammetry based on hydrogen absorption (underpotential deposition). The measurements were carried out in 0.5 M $H_2SO_4$ and 1 mm $CuSO_4$ as an electrolyte. The measured sample surface area was limited to 10 mm² by covering with Kapton foil. Measurements were carried out from 0.3 V to 1.3 V at a scan rate of 20 mV/s. The average of 17 measurements was taken.

An active surface area of 387 mm² was thereby determined. Based on the measured sample volume of approximately 0.005 mm³ (10 mm² area, approximately 500 nm thickness), the specific surface area is $7.72 \times 10^7$ m⁻¹ (i.e., approximately 77,200,000 m⁻¹).

FIGURES

FIG. 1 shows an example of an embodiment of an electrode according to the invention in a cross-sectional view. A first layer 102 is arranged on the substrate 101. A second layer 103 comprising a conductive polymer is arranged on the first layer 102. The first layer 102 comprises a noble metal and comprises a porous and/or rough surface at the interface with the second layer 103.

Figure 2:
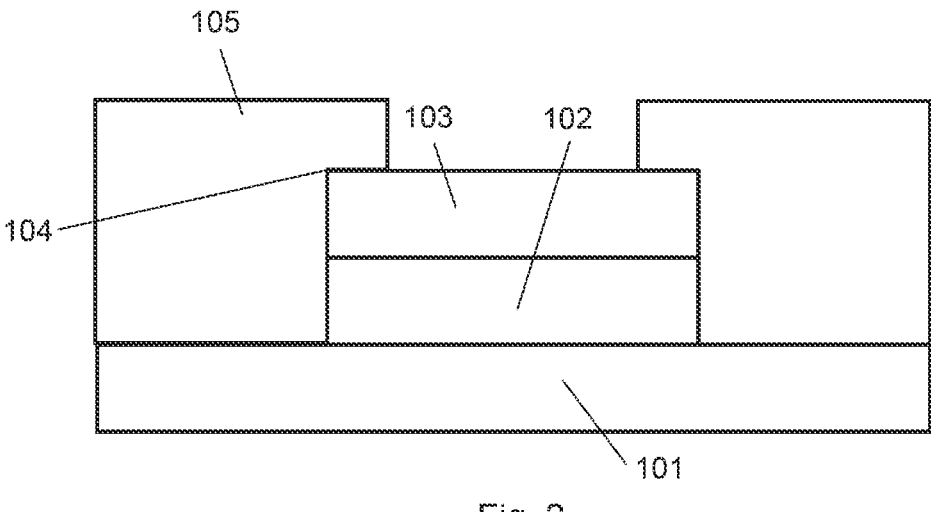
FIG. 2 shows an example of a further embodiment of an electrode according to the invention in a cross-sectional view.

FIG. 2 shows an example of a further embodiment of an electrode according to the invention in a cross-sectional view. Similar to the embodiment shown in FIG. 1, the electrode comprises a substrate 101 covered by a first layer 102 and a second layer 103. The first layer 102 comprises a noble metal. The second layer 103 comprises a conductive polymer, such as PEDOT. Additionally, the electrode includes an edge 104 of the second layer 103, which is covered by a third layer 105. In the example shown here, the third layer 105 laterally seals both the first layer 102 and the second layer 103 to the outside. In this manner, the stability of the first layer 102 and/or the second layer 103 can be further improved. In the example shown here, the substrate 101 comprises the plastics material polyimide.

Figure 3A:
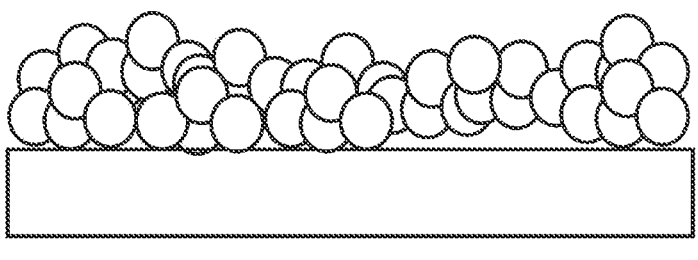
FIGS. 3*a*-3*b* show an example of a further embodiment of an electrode according to the invention in a cross-sectional view.
Figure 3B:
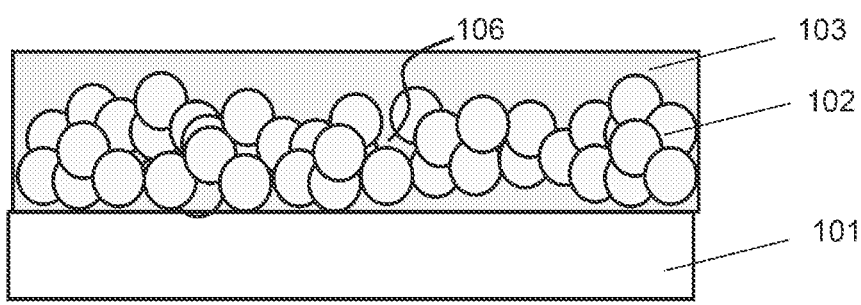

FIGS. 3*a*-3*b* show an example of a further embodiment of an electrode according to the invention in a cross-sectional view. A substrate 101 is at least partially covered by a first layer 102 comprising a noble metal. A second layer 103 comprising a conductive polymer is arranged on the first layer 102. The first layer 102 comprises recesses 106. The material of the second layer 103 engages the recesses 106 of the first layer 102, such that the first layer 102 is interlocked with the second layer 103. The recesses have a width in the nanometer range.

Figures 4A, 4B, 4C:
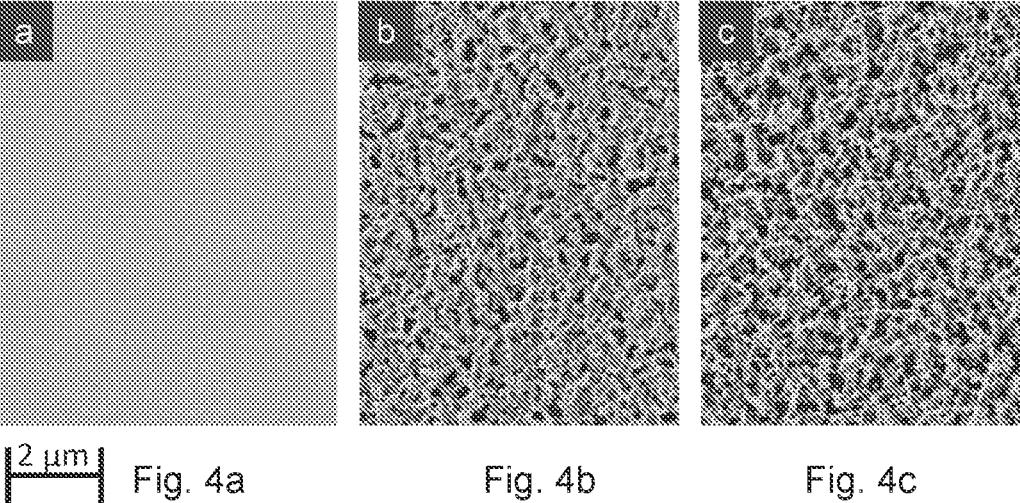
FIGS. 4*a*-4*c* show SEM images of monolayers that differ from one another due to their density or porosity.

FIGS. 4*a*-4*c* show SEM images of monolayers that differ from one another due to their density or porosity. The layer on the left (FIG. 4*a*) shows a layer containing platinum in metallic form, obtained by means of coating a substrate (polyimide) with a composition containing the PtV complex dissolved in propylene glycol n-propyl ether (PnP) and subsequent thermal decomposition of the complex at a temperature of 200° C. The layer in the middle (FIG. 4*b*) shows a layer containing platinum in metallic form, obtained by coating a substrate (polyimide) with a composition containing the PtV complex in a mixture (1:1) of PnP and ethanol and subsequent thermal decomposition of the complex at a temperature of 250° C. The layer on the right (FIG. 4*c*) shows a layer containing platinum in metallic form, obtained by means of coating a substrate (polyimide) with a composition containing the PtE complex in a mixture of PnP and ethanol (1:1) and subsequent thermal decomposition of the complex at a temperature of 220° C. The porous structures in FIG. 4*b* and FIG. 4*c* each clearly show recesses on their surface area, the width of which is in an order of magnitude of approximately 10 nm to 1000 nm.

Figure 5:
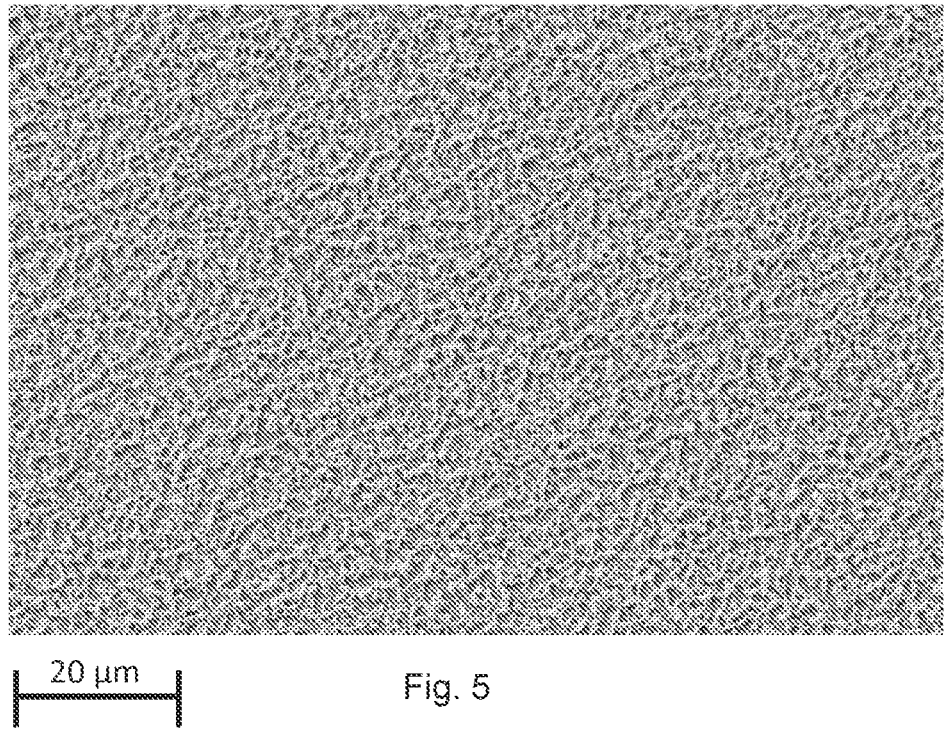
FIG. 5 shows a platinum layer produced by means of inkjet printing using a platinum ink with PtE complex.

FIG. 5 shows a platinum layer produced by means of inkjet printing using a platinum ink with PtE complex. The layer shown is thinner than the layers shown in FIG. 4*b* and FIG. 4*c*. This clearly shows the underlying substrate layer. The printed platinum layer forms a mesh-like structure, which continuously covers the surface area of the substrate, and comprises practically no isolated platinum particles. At the same time, it has a large specific surface area. There are numerous interstices within the mesh structure. Such a printed platinum layer combines good electrochemical properties, such as lower impedance, with good adhesion properties with respect to a polymer layer, such as Amplicoat and similar PEDOT-based compositions, applied thereon.

Figure 6:
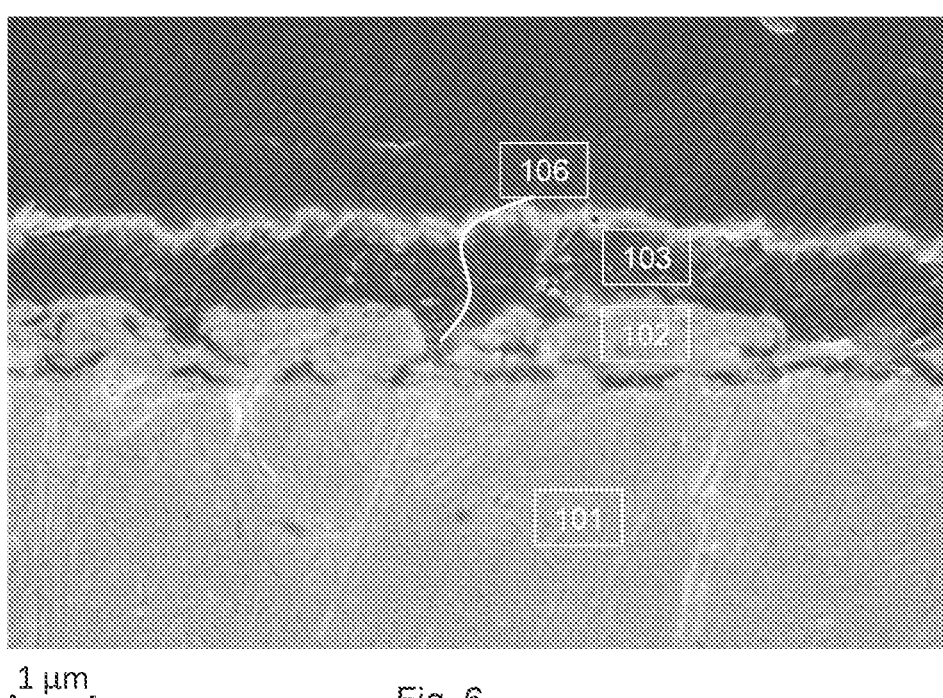
FIG. 6 shows a cross-sectional electron microscope view of an electrode according to the invention.

FIG. 6 shows a cross-sectional electron microscope view of an electrode according to the invention. A porous platinum layer 102, which was produced by means of inkjet printing using a platinum ink with PtE complex, is arranged on a substrate 101 made of platinum-iridium. This porous platinum layer 102 is covered with a polymer layer 103 of Amplicoat. Similar to what is shown in FIG. 3, the porous platinum layer 102 comprises recesses 106 that are filled with the polymer of the second layer 103, such that the first layer 102 and the second layer 103 interlock with each other, such that a microscopic form-fitting bond is formed between the first layer 102 and the second layer 103, resulting in improved stability of the two layers.

Figure 7:
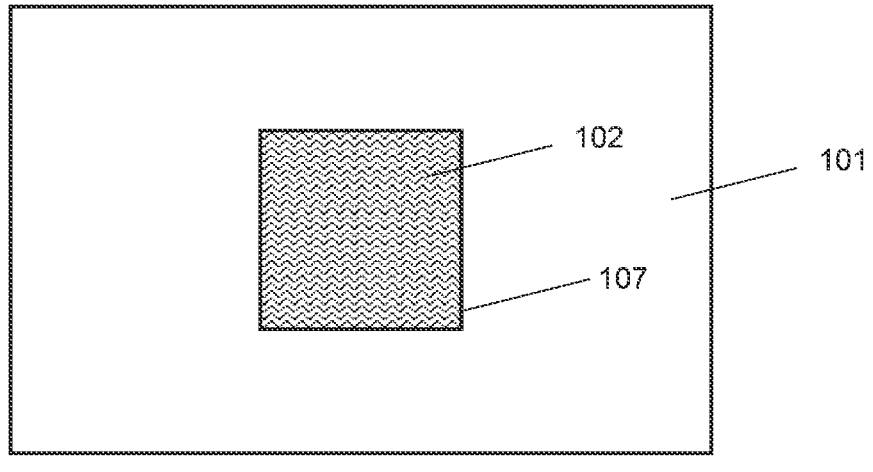
FIG. 7 schematically shows the determination of the proportional surface area coverage by the applied first layer.

FIG. 7 schematically shows the determination of the proportional surface area coverage by the applied first layer. For this purpose, a macroscopically closed region 107 is initially determined, which comprises parts of the first layer 102. This region 107 in turn comprises covered and uncovered portions on a microscopic scale, which define the surface area coverage.

For example, if a square area, i.e., a portion of the surface area of the substrate 101, is printed with a platinum ink, this region 107 corresponds exactly to this printed area. The remaining unprinted surface area parts of the substrate 101 are not included in the determination of surface area coverage, but the microscopic "gaps" within this region 107 are. Accordingly, the surface area coverage of the first layer of the substrate herein always refers to the portion of the substrate surface area within the "macroscopic" region 107 defined as above that is covered by the first layer, i.e., not necessarily the entire substrate surface area.

The invention claimed is:

1. A medical electrode comprising a substrate, a first layer, and a second layer, wherein the first layer is arranged directly on the substrate, and the second layer is arranged directly on the first layer, wherein the first layer comprises a noble metal applied in multiple layers as particle-free noble metal ink on the substrate and thermally decompositioning the particle-free noble metal ink, and the second layer comprises a conductive polymer, characterized in that the first layer comprises one or more of the following features (a) to (e):

(a) an open-pore structure,
  (b) a porosity of at least 30% by volume,
  (c) a density of at most 90% of the theoretical density of the noble metal,
  (d) a specific surface area of at least $1 \times 10^6$ m$^{-1}$,
  (e) an average surface roughness Ra of at least 500 nm.

2. The medical electrode according to claim 1, wherein the first layer further comprises one or more of the following features:

a charge storage capacity of at least 10 mC/cm$^2$,
  an impedance of at most 1500 $\Omega$,
  wherein the specified features are to be determined on an area of the first layer of 5 mm$^2$,
  and in the absence of the second layer.

3. The medical electrode according to claim 1, wherein the substrate comprises a noble metal or a biocompatible plastics material.

4. The medical electrode according to claim 1, wherein the first layer comprises a noble metal that is selected from the group consisting of platinum, iridium, palladium, gold, ruthenium, and rhodium.

5. The medical electrode according to claim 1, wherein the second layer comprises PEDOT.

6. The medical electrode according to claim 1, wherein the first layer covers at least 5% of the surface area of the substrate.

7. The medical electrode according to claim 1, wherein the second layer intercalates with the first layer.

8. The medical electrode according to claim 1, wherein the second layer comprises an edge that is covered by a third layer.

9. The medical electrode according to claim 1, wherein the first layer can be produced by thermal decomposition of a particle-free noble metal ink.

10. A method for producing a medical electrode, comprising:

provision of a substrate,
  multiple applications of a particle-free noble metal ink to the substrate,
  thermal decomposition of the noble metal ink in order to obtain a first layer of noble metal,
  application of a conductive polymer to the first layer in order to obtain a second layer.

11. The method according to claim 10, wherein the noble metal ink comprises an organic noble metal complex having diolefin and C6-C18 monocarboxylate ligands of the type [LPd[O(CO)R1]X]$_n$, [LRh[O(CO)R1]]$_m$ or [LIr[O(CO)R1]]$_m$, wherein L is a compound acting as a diolefin ligand, wherein X is selected from bromide, chloride, iodide and —O(CO)R2, wherein —O(CO)R1 and —O(CO)R2 denote identical or different non-aromatic C6-C18 monocarboxylic acid functional groups, and wherein n is an integer $\geq 1$ and m is an integer $\geq 2$.

12. The method according to claim 11, wherein the noble metal complex is a compound of the formula [(L1L2)Pt[O(CO)R$^1$]$_2$]$_n$, wherein n is equal to 1 or 2, L1L2 is cyclooctadiene or norbornadiene, and wherein R$^1$ is a non-aromatic C7-C17 hydrocarbon functional group.

13. The method according to claim 10, wherein the noble metal ink comprises a solvent, which comprises propylene glycol n-propyl ether and/or ethanol.

14. The method according to claim 10, wherein a plurality of layers of a noble metal are successively applied, each by means of a particle-free noble metal ink.

15. The method according to claim 10, wherein the noble metal ink/inks is/are applied by means of inkjet printing, screen printing, stamp printing, dispensing, dip coating, spray coating or spin coating.

\* \* \* \* \*